United States Patent [19]
Hartley, deceased,

[11] Patent Number: 5,388,129
[45] Date of Patent: Feb. 7, 1995

[54] APPARATUS AND METHOD FOR RADIOGRAPHIC INSPECTION OF WELDS

[75] Inventor: James L. Hartley, deceased, late of Glenshaw, Pa., by Margaret C. Hartley, Executrix

[73] Assignee: Westinghouse Electric Corporation, Pittsburgh, Pa.

[21] Appl. No.: 114,406

[22] Filed: Sep. 1, 1993

[51] Int. Cl.⁶ .......................................... G21C 17/00
[52] U.S. Cl. ..................................... 376/249; 376/159
[58] Field of Search .............. 376/249, 251, 451, 159; 250/390.02, 497.1; 976/DIG. 236

[56] References Cited

U.S. PATENT DOCUMENTS

| | | | |
|---|---|---|---|
| 3,222,524 | 12/1965 | Lee | 250/496.1 |
| 3,612,874 | 10/1971 | Porter | 250/83.1 |
| 3,666,944 | 5/1972 | Baldinger | 250/65 R |
| 4,078,180 | 3/1978 | Green | 250/358 R |
| 4,491,731 | 1/1985 | Funyu et al. | 250/358.1 |
| 4,516,256 | 5/1985 | Wapperom | 378/60 |
| 4,554,128 | 11/1985 | Parker et al. | 376/252 |
| 4,567,012 | 1/1986 | Radcliff | 376/245 |
| 4,924,481 | 5/1990 | Vaughn | 378/59 |
| 5,249,209 | 8/1993 | Kwech | 376/260 |

FOREIGN PATENT DOCUMENTS

| | | |
|---|---|---|
| 53-28052 | 3/1978 | Japan . |
| 55-50998 | 4/1980 | Japan . |
| 1195620 | 6/1970 | United Kingdom . |
| 2042860 | 9/1980 | United Kingdom . |
| 2064929 | 6/1981 | United Kingdom . |
| 322707 | 2/1972 | U.S.S.R. . |
| 421882 | 8/1974 | U.S.S.R. . |
| 936533 | 5/1982 | U.S.S.R. . |

Primary Examiner—Donald P. Walsh
Assistant Examiner—Meena Chelliah
Attorney, Agent, or Firm—Walter S. Stevens

[57] ABSTRACT

Apparatus and method for radiographic inspection of welds, which welds may be seal welds of the kind typically found on nuclear power reactor control rod drive mechanisms (CRDMs). Such CRDM seal welds seal the threaded joint defined by a generally tubular pressure housing and a generally tubular vessel head adapter, the housing and adapter enclosing the CRDM components. The apparatus comprises a circular track capable of surrounding and being connected to the vessel head adapter. A radiation source assembly capable of emitting penetrating radiation and a radiation shielding assembly capable of shielding against the radiation are mounted on the track. The assemblies are adjustable for aligning the assemblies with the seal weld. A radiographic film is interposed between the radiation source assembly and the radiation shielding assembly and adjacent the weld for capturing a volumetric image of the weld on the film. A collimated beam of penetrating radiation is emitted from the radiation source assembly along an axis passing tangentially through the seal weld and through the film for suitably radiographing relatively small pinhole-sized anomalies in the weld.

21 Claims, 9 Drawing Sheets

APPARATUS AND METHOD FOR RADIOGRAPHIC INSPECTION OF WELDS

BACKGROUND

This invention generally relates to apparatus and methods for inspection of welds and more particularly relates to apparatus and methods for radiographic inspection of welds, which welds may be seal welds of the kind typically found on nuclear power reactor control rod drive mechanisms.

Although devices and methods for radiographing welds are known in the prior art, it has been observed that prior art devices and methods have certain operational problems associated with them which make these devices and methods unsuitable for radiographing welds of the kind typically found on nuclear power reactor control rod drive mechanisms. However, before these problems can be appreciated, some background is necessary as to the structure and operation of a typical nuclear power reactor and its associated control rod drive mechanism.

In this regard, a nuclear power reactor is a device for producing heat by the controlled fission of fissionable material contained in fuel rods. A plurality of the fuel rods are bundled together by a plurality of spaced-apart grids, each grid having open fuel rod cells for receiving each fuel rod therethrough. Each grid also has open guide tube cells for receiving respective ones of a plurality of control rod guide tubes. Each control rod guide tube is in turn capable of slidably receiving a movable control rod for controlling the fission process in the nuclear reactor. The fuel rods, control rod guide tubes and grids define a fuel assembly, a plurality of which fuel assemblies are grouped in a sealed reactor pressure vessel to define a nuclear reactor core. Pressurized liquid moderator coolant (i.e., borated demineralized water) is caused to circulate through the pressure vessel and over the fuel rods in the reactor core for assisting in the fission process and for removing the heat produced by fission of the fissionable material contained in the fuel rods.

Clusters of the previously mentioned movable control rods are each connected to a control rod drive mechanism (CRDM) which is attached to the top of the reactor pressure vessel. The CRDMs are capable of selectively vertically positioning the control rods within the fuel assemblies to adjust the core reactivity so that the fission process is suitably controlled thereby. For this purpose, the control rods that are connected to the CRDMs can be withdrawn from or inserted into the core by the CRDMs at speeds consistent with the reactivity changes required for controlling the fission process. Thus, during normal reactor operation, the CRDMs serve to axially move or to hold in position the control rods that have been withdrawn from the reactor core for sustaining the fission process.

The moving internal components of each CRDM, which is capable of moving the control rod cluster connected thereto, are contained in a pressure housing attached to the top of a reactor vessel head adaptor, which is in turn attached to the top of the reactor pressure vessel. The pressure housing is threadably connected to the vessel head adaptor and seal welded thereat for sealing the joint defined by the threaded connection. The pressurized reactor coolant previously mentioned fills the pressure vessel head adaptor and the pressure housing and immerses all moving components of the CRDM to serve as lubricant for the CRDM components. Thus, the vessel head adaptor, which is attached to the top of the reactor pressure vessel (i.e., attached to the reactor pressure vessel closure head), forms part of the pressure boundary of the reactor pressure vessel. Consequently, in the typical nuclear reactor, the pressure housing and the vessel head adaptor are designed for full system pressure of approximately 2500 pounds per square inch absolute (psia).

Applicant has observed that, due to weld degradation, small pinhole leaks of borated coolant have occurred at the location of the seal welds sealing the threaded joint defined by the pressure housing and the reactor vessel head adaptor. Such a CRDM pressure housing leak ultimately could lead to undesirable reactivity anomalies in the reactor core because the inventory of the borated moderator coolant used to assist in controlling the fission process is momentarily reduced by the leak. In addition, because the pressure housing of the CRDM forms a portion of the reactor pressure boundary, any seal weld leaks may affect the pressure and thus the temperature of the moderator coolant. Variation in the coolant temperature also undesirably affects core reactivity. Such leaks might also cause corrosion of the low alloy base metal comprising the pressure housing of the CRDM and may thereby compromise the structural integrity of the CRDM. Although the precise cause of the weld degradation is unknown, it is believed that the factors contributing to such leaks may be faulty welding or contaminants in the weld. Moreover, the process of welding the consumable filler inserts used to form the seal welds during the welding process may result in an insufficient amount of filler metal being deposited. Furthermore, the weld anomalies could also be related to improper weld temperature control or insufficient gas purging at the locus of the weld during the welding process. In addition, the weld degradation may be related to thermal cycling which the welds might undergo during reactor heat-up and cool-down.

Degraded seal welds are repaired by overlaying the seal weld with additional filler material, the repaired weldment then being subjected to grinding to produce a smooth weld. However, it has been observed by applicant that such a repaired weld may also leak if there is insufficient fusion of the filler and base metals or if the weldment is excessively ground and then subjected to the relatively high system pressure of normal reactor operation.

It is therefore important to inspect the seal welds that seal the threaded joint between the pressure housing and the vessel head adaptor to detect any weld anomalies that might lead to leakage of the coolant. It is prudent to perform this inspection even after any weld anomalies have been repaired in order to confirm the sufficiency of the repair. In this regard, it is current practice in the art to visually inspect the exterior surfaces of seal welds on approximately ten percent of the CRDMs during hydrostatic tests. In the case of visual inspection, the American Society of Mechanical Engineers (ASME) Code requires that there must be sufficient access to the weld to allow the eye to be within 24 inches of the exterior surface of the weld and at an angle not less than 30 degrees to the surface inspected. Mirrors can be used to improve the angle of vision. The ASME Code also allows use of a remote camera for visual examination of the seal welds; but, the remote camera systems must have a resolution capability as good as obtainable by direct visual inspection. However, applicant has observed that visual inspection techniques may not obtain the required level of reliability because such techniques are inherently dependent on the visual acuity of the maintenance personnel performing the visual inspection. In addition, in many cases visual examination of exposed surfaces cannot detect locations of impending leaks due to subsurface weld anomalies.

Ultrasonic examination may be used to detect subsurface weld anomalies such as subsurface cracks, local thinning, or other anomalies. Moreover, dye penetrant inspections, magnetic particle testing, and eddy current inspection may also be used to detect subsurface weld anomalies. However, it has been observed by applicant that use of these devices and methods is time consuming and generally lack the required sensitivity and are therefore unsuitable for reliably detecting relatively small pinhole anomalies in the seal weld.

Prior art methods have been used to detect anomalies both on the surface and in the subsurface of welds. A method of radiographic inspection of a joint formed between an end-cap and a tubular can which forms part of a nuclear fuel element is disclosed in British Patent 1,195,620 titled "Method of Inspection of Welds" published Jun. 17, 1970 in the name of Pierre Soulat. This patent discloses that to inspect the welded joint between a tube and its end cap, the tube is continuously rotated about its axis at a peripheral linear speed equal to the speed at-which a film, detecting the X-rays after passage through the tube, is displaced tangentially to the tube, the X-ray beam being directed perpendicularly to the film. Although the Soulat patent may disclose a method of radiographic inspection of a welded joint, the Soulat method apparently requires that the workpiece be rotated in order to perform the inspection. Thus, the Soulat patent does not appear to disclose an apparatus and method for suitably radiographing CRDM seal welds because the CRDM is stationary.

X-ray equipment for mechanized testing of the integrity of welds along the length of the welds is disclosed in U.S. Pat. No. 4,078,180 titled "X-Ray Inspection of Welds" issued Mar. 7, 1978 in the name of Donald T. Green. This patent discloses means for mechanically traversing an X-ray source along one side of the weld and a grainless fluorescent screen along the other side, with the screen coupled to an image-isocon video camera. According to this patent, photographic film or magnetic tape can be substituted for the camera. More specifically, this patent discloses an X-ray tube inserted in a pipe and projecting a conical X-ray beam through the weld in the wall of the pipe. On the outside of the pipe facing the X-ray tube is a fluoroscopic screen placed close to the outside of the pipe to obtain a picture of the flaw in the weld. Although the Green patent may disclose X-ray equipment for testing the integrity of welds, this patent does not appear to disclose an apparatus and method for suitably radiographing relatively small pinhole-sized anomalies in CRDM seal welds.

Therefore, what is needed is an apparatus and method for radiographing a weld, which weld may be a seal weld of the kind typically found on nuclear power reactor control rod drive mechanisms.

SUMMARY

Disclosed herein are an apparatus and a method for radiographic inspection of welds, which welds may be seal welds of the kind typically found on nuclear power reactor control rod drive mechanisms (CRDMs). Such CRDM seal welds seal the threaded joint defined by a generally tubular pressure housing and a generally tubular reactor vessel head adapter, the housing and adapter enclosing the CRDM components. The apparatus comprises a circular track adapted to surround the vessel head adapter. A radiation source assembly capable of emitting penetrating radiation and a radiation shielding assembly capable of shielding against the radiation are mounted on the track. The assemblies are adjustable on the track for aligning the assemblies with the seal weld. A radiographic film is interposed between the radiation source assembly and the radiation shielding assembly and adjacent the weld for obtaining an volumetric radiographic image of the weld. A collimated beam of penetrating radiation is emitted from the radiation source assembly along an axis passing obliquely tangentially through the seal weld and through the film for suitably radiographing relatively small pinhole-sized anomalies in the weld.

In its broad form, the invention is an apparatus for radiographic inspection of a weld circumscribing opposing ends of a tubular first member and a tubular second member, the apparatus comprising a track surrounding one of the members, radiation source means mounted on the track for passing a beam of radiation tangentially through the weld, and radiation shielding means mounted on the track for providing a shield against the beam of radiation. The invention in its broad form is also a method of radiographic inspection of the weld, the method comprising the steps of surrounding one of the members with the track, mounting a radiation source on the track so that the beam of radiation emitted by the radiation source passes tangentially through the weld, and mounting a radiation shield on the track so that the beam of radiation is shielded against.

An object of the present invention is to provide an apparatus and a method for radiographic inspection of welds, which welds may be seal welds of the kind typically found on nuclear power reactor control rod drive mechanisms.

Another object of the present invention is to provide an apparatus and method for passing a beam of penetrating radiation tangentially through a circularly extending weld rather than perpendicularly through the weld.

A feature of the present invention is the provision of radiation source means for emitting a beam of penetrating radiation and radiation shielding means for shielding against the radiation, the source means and the shielding means being mountable on a track surrounding the weld such that the beam of radiation passes tangentially through the weld.

An advantage of the present invention is that seal welds of the kind typically found on CRDMs can be suitably radiographed by use of the invention so that relatively small pinhole-sized anomalies in the weld can be detected.

These and other objects, features, and advantages of the present invention will become apparent to those skilled in the art upon a reading of the following detailed description when taken in conjunction with the drawings wherein there is shown and described illustrative embodiments of the invention.

BRIEF DESCRIPTION OF THE DRAWINGS

While the specification concludes with claims particularly pointing out and distinctly claiming the subject matter of the invention, it is believed the invention will be better understood from the following description, taken in conjunction with the accompanying drawings wherein:

DESCRIPTION OF THE PREFERRED EMBODIMENT(S)

Disclosed hereinbelow are an apparatus and a method for radiographic inspection of welds, particularly seal welds of the kind typically found on nuclear power reactor control rod drive mechanisms (CRDMs). A CRDM comprises a pressure housing threadably connected to a vessel head adaptor, the pressure housing and the vessel head adaptor being joined by a circumscribing seal weld to seal the threaded joint defined thereby. On occasion, such a seal weld may degrade and develop pinhole-sized leaks that could ultimately lead to reactivity anomalies in the reactor core. Such pinhole leaks may also compromise the structural integrity of the CRDM by corroding the base metal of the CRDM. It is therefore desirable to inspect such seal welds for anomalies that could lead to leaks.

According to the invention, such inspection is performed by a suitable radiographic apparatus and method.

However, before describing the subject matter of the present invention, it is instructive first to briefly describe the structure and operation of a typical nuclear power reactor and associated control rod drive mechanism.

Figure 1:
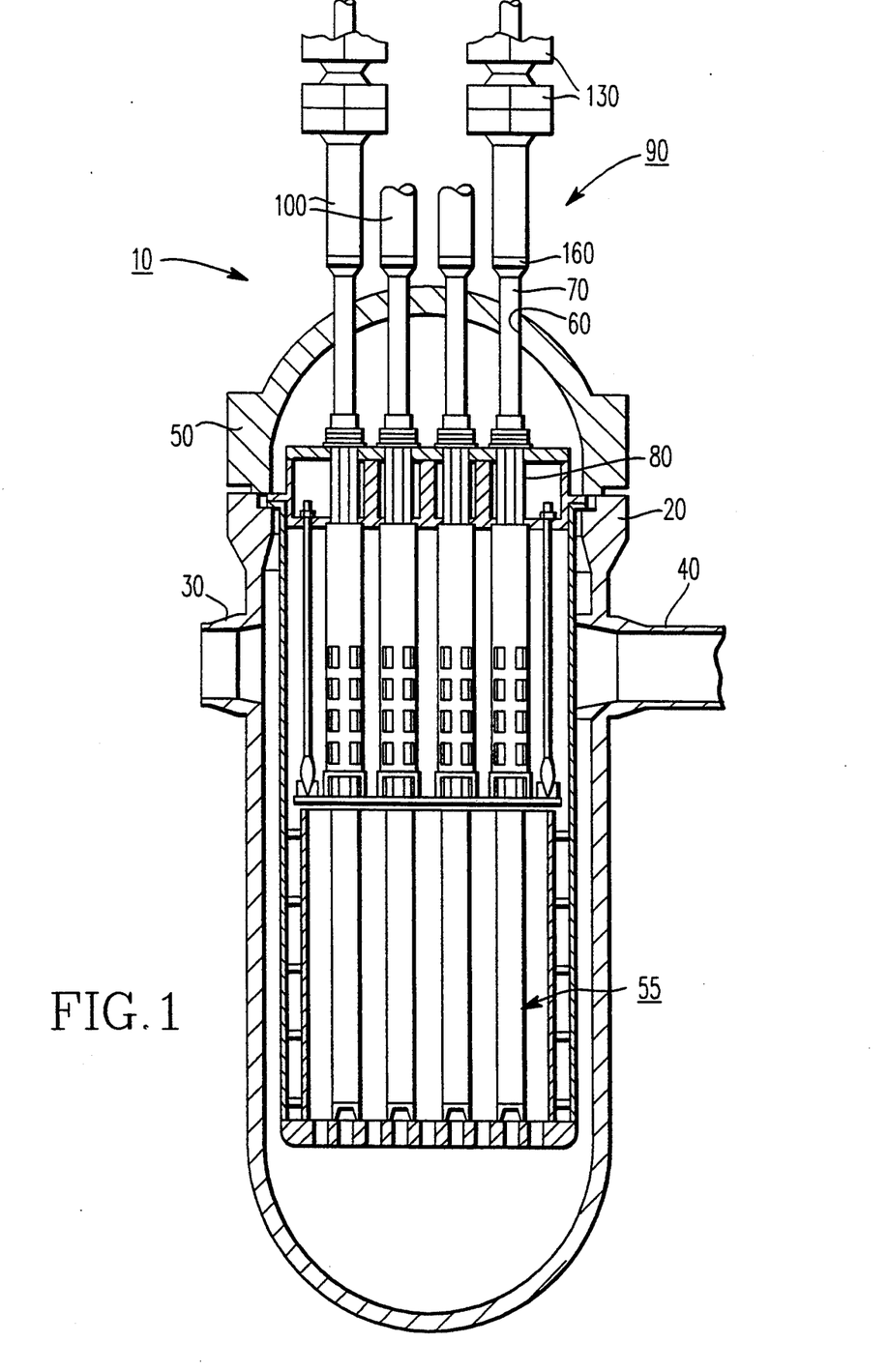
FIG. 1 shows in partial vertical section, a typical nuclear reactor pressure vessel with parts removed for clarity, the pressure vessel having a plurality of Control Rod Drive Mechanisms (CRDMs) attached thereto, each CRDM comprising a pressure housing threadably engaging and sealingly welded to a reactor vessel head adaptor.

Therefore referring to FIG. 1, there is shown a typical nuclear power reactor, generally referred to as 10, for producing heat by the controlled fission of fissionable material. Reactor 10 includes a reactor pressure vessel shell 20 open at its top end and having a plurality of inlet nozzles 30 and outlet nozzles 40 attached to the upper portion thereof (only one of each nozzle is shown). A hemispherical reactor vessel closure head 50 is mounted atop vessel shell 20 and is sealingly attached, which may be by bolting, to the open top end of vessel shell 20 so that closure head 50 sealingly caps vessel shell 20. Capping vessel shell 20 in this manner allows for suitable pressurization of the coolant (not shown) circulating through vessel shell 20 as reactor 10 operates. This coolant may be borated demineralized water at a system pressure of approximately 2500 psia and a system temperature of approximately 650 degrees Fahrenheit.

Still referring to FIG. 1, disposed in reactor 10 is a nuclear reactor core, generally referred to as 55, comprising a plurality of nuclear fuel rods (not shown) containing fissionable material (also not shown). Formed through the top of closure head 50 are a plurality of closure head openings 60 for receiving respective ones of a plurality of generally tubular reactor vessel head adapters 70. Each vessel head adaptor 70 has an end portion 73 having external threads 75 therearound (see FIG. 3). With reference to FIG. 1, vessel head adaptor 70 houses a control drive shaft (not shown) extending through each vessel head adaptor 70, the drive shaft engaging at least one movable drive rod 80. Vessel head adaptor 70 may be made from corrosion resistant Type 304 stainless steel which comprises by weight percent approximately 0.08% carbon, 20% chromium, 11% nickel, and 68.92% iron. Moreover, integrally attached to end portion 73 and outwardly projecting therefrom is an upwardly curved, bowl-shaped canopy or flange 77 surrounding end portion 73, flange 77 having an upwardly facing edge 79 (see FIG. 3) for reasons disclosed hereinbelow. Drive rod 80 is in turn connected to a control rod cluster (not shown) for controlling the fission process in reactor core 55.

Figures 2, 3:
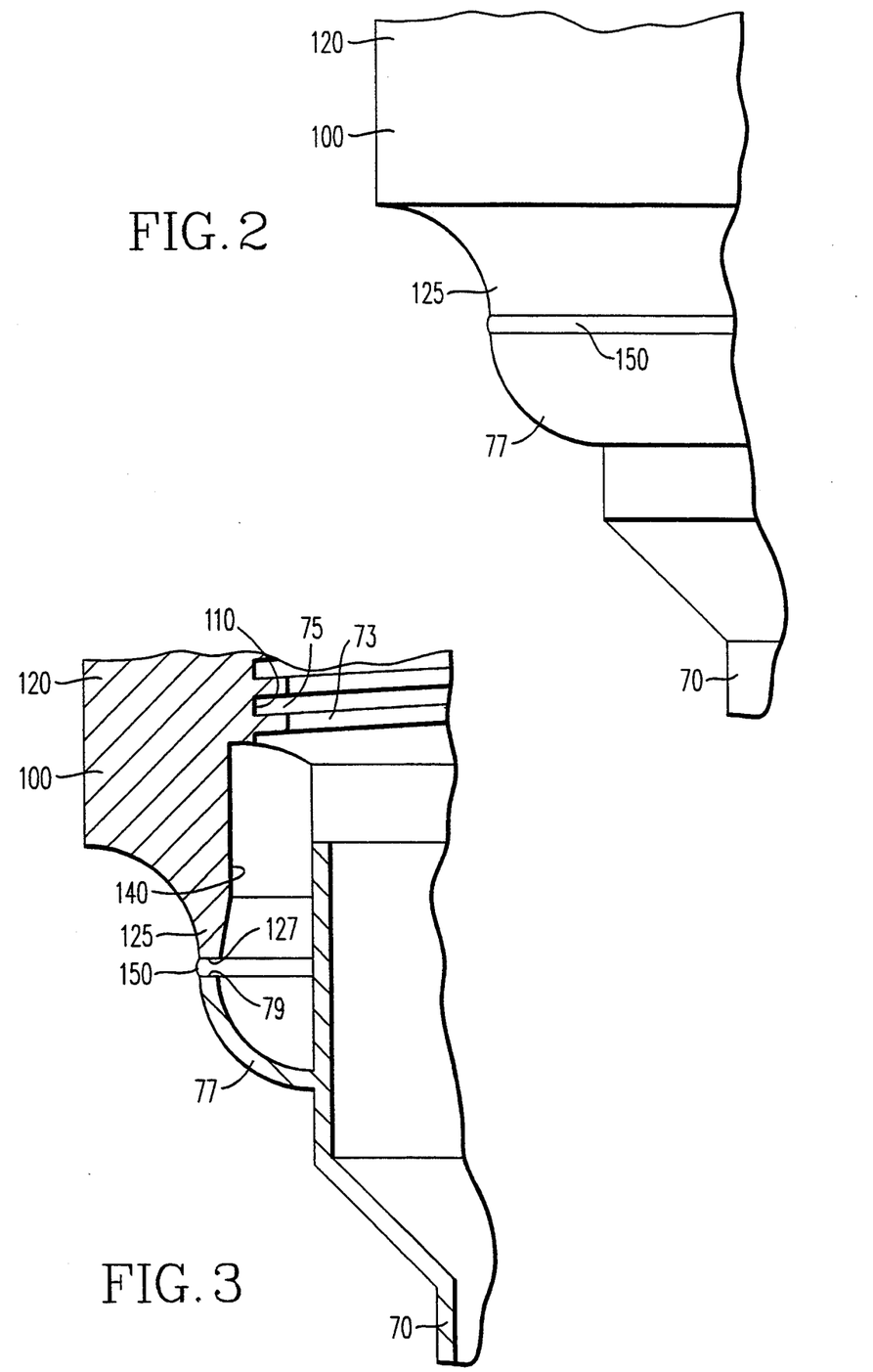
FIG. 2 shows in elevation, the pressure housing engaging and sealingly welded to the reactor vessel head adaptor.
FIG. 3 shows in partial elevation, the pressure housing threadably engaging and sealingly welded to the reactor vessel head adaptor.
Figure 4:
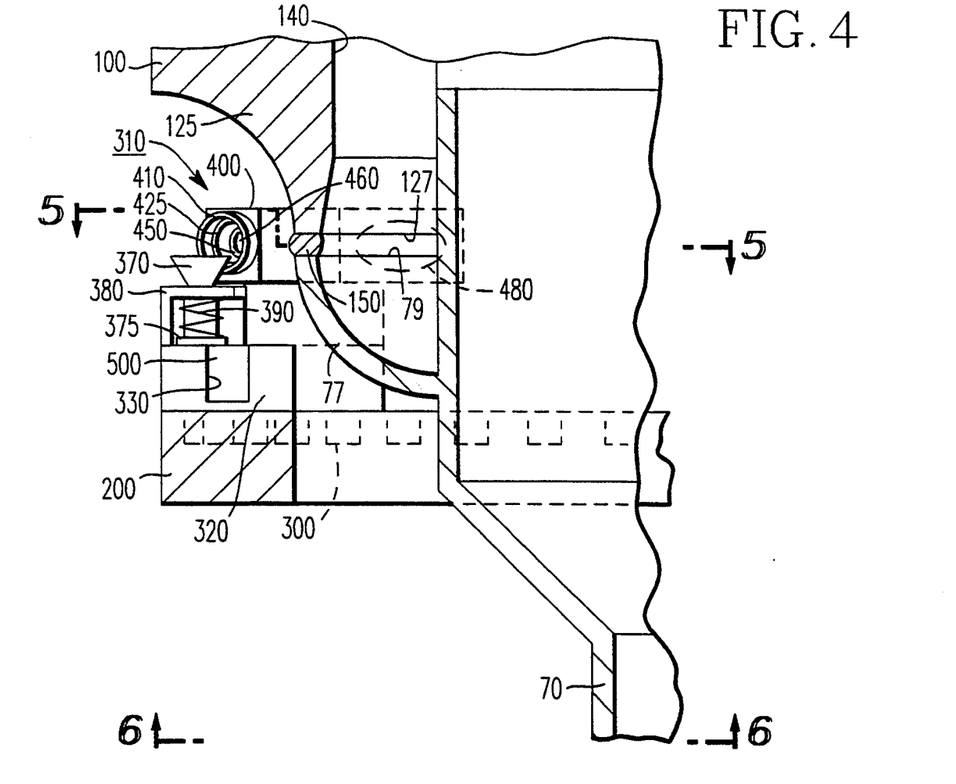
FIG. 4 shows in partial elevation, the apparatus of the invention disposed in operative condition to radiograph the seal weld surrounding the threaded joint defined by the pressure housing and vessel head adaptor.

Referring to FIGS. 1, 2, and 3, threadably engaging vessel head adaptor 70 is a control rod drive mechanism (CRDM), generally referred to as 90, for axially moving drive rod 80 and thus the control rod cluster connected thereto. CRDM 90 comprises a generally tubular pressure housing 100, which may be Type 304 stainless steel, having internal threads 110 at an end portion 120 thereof for threadably engaging the external threads 75 of vessel head adaptor 70. End portion 120 includes an integrally attached lip 125 having a downwardly facing bottom edge 127, for reasons disclosed hereinbelow. Attached to pressure housing 100 and surrounding the exterior surface thereof are a plurality of electromagnetic coil stack assemblies 130 for electromagnetically axially moving drive rod 80 as coil stack assemblies 130 are electrically energized.

Referring to FIGS. 2 and 3, the bottom edge 127 of lip 125 belonging to pressure housing 100 is disposed immediately above and adjacent top edge 79 belonging to flange 77. Lip 125 and flange 77 generally define a cavity 140 therebetween surrounding the threaded connection of pressure housing 100 and vessel head adaptor 70. Interposed between and joining bottom edge 127 of lip 125 to top edge 79 of flange 77 is a seal weld 150. Seal weld 150 extends circumferentially around bottom edge 127 and top edge 79 for defining a welded joint therebetween. When seal weld 150 completely circumscribes or surrounds bottom edge 127 and top edge 77, seal weld 150 seals cavity 140 for sealing the threaded joint defined by pressure housing 100 and vessel head adaptor 70.

Turning now to FIGS. 4, 5, 5A, 6, 6A, 7, 8 and 9, there is shown the subject matter of the present invention, which is an apparatus, generally referred to as 190, for inspecting a weld, such as seal weld 150. Apparatus 190 comprises a circular track 200 adapted to surround end portion 73 of vessel head adaptor 70. Integrally connected to an underside 210 of track 200 is support means, such as a plurality of equally spaced-apart support struts 220, for supporting track 200 on the exterior surface of vessel head adaptor 70. Each support strut 220 depends from underside 210 of track 200 at a predetermined angle, which may be approximately 45 degrees, depending on the outside diameter of vessel head adaptor 70. An integrally attached end portion 230 of strut 220 has an adjustable clamp member 250 for clamping track 200 to vessel head adaptor 70. Clamp member 250 may comprise a screw 250 extending threadably through end portion 230 and terminating in a foot-pad 260 adapted to abut the exterior surface of vessel head adaptor 70. Foot-pad 260 may have a non-slip surface, such as made of a suitable non-slip rubber, for abutting or engaging the exterior surface of vessel head adaptor 70, the non-slip surface having a relatively high coefficient of friction when engaging the exterior surface of vessel head adaptor 70. Such a non-slip surface prevents track 200 from sliding downwardly on the exterior surface of vessel head adaptor 70. It will be appreciated from the above description that turning screw 250 in one direction adjustably advances foot-pad 260 into abutting relationship with the exterior surface of vessel head adaptor 70 and turning screw 250 in the opposite direction retracts foot-pad 260 out of abutment with the exterior surface of vessel head adaptor 70. In this manner, track 200 can be removably adjustably connected to vessel head adapters of varying outside diameters.

As best seen in FIGS. 5, 5A, 6 and 7, track 200 includes a plurality of hinged segments, such as segments 270a and 270b, for allowing track 200 to removably surround vessel head adaptor 70. In this regard, segments 270a and 270b are connected by a hinge 280 for rotating segments 270a and 270b about hinge 280 into an open configuration prior to positioning track 200 about vessel head adaptor 70 and for bringing segments 270a and 270b into a closed configuration, as shown in the several figures, to surround vessel head adaptor 70 in order to position track 200 about vessel head adaptor 70. Track 200 also includes fastener means, which may be a screw-like fastener 290, for fastening segments 270a and 270b together, once they are brought into a closed configuration around vessel head adaptor 70. Moreover, the preferred embodiment of track 200 includes a plurality of equally spaced-apart transverse bores 300 therearound, for reasons disclosed hereinbelow.

Figure 5:
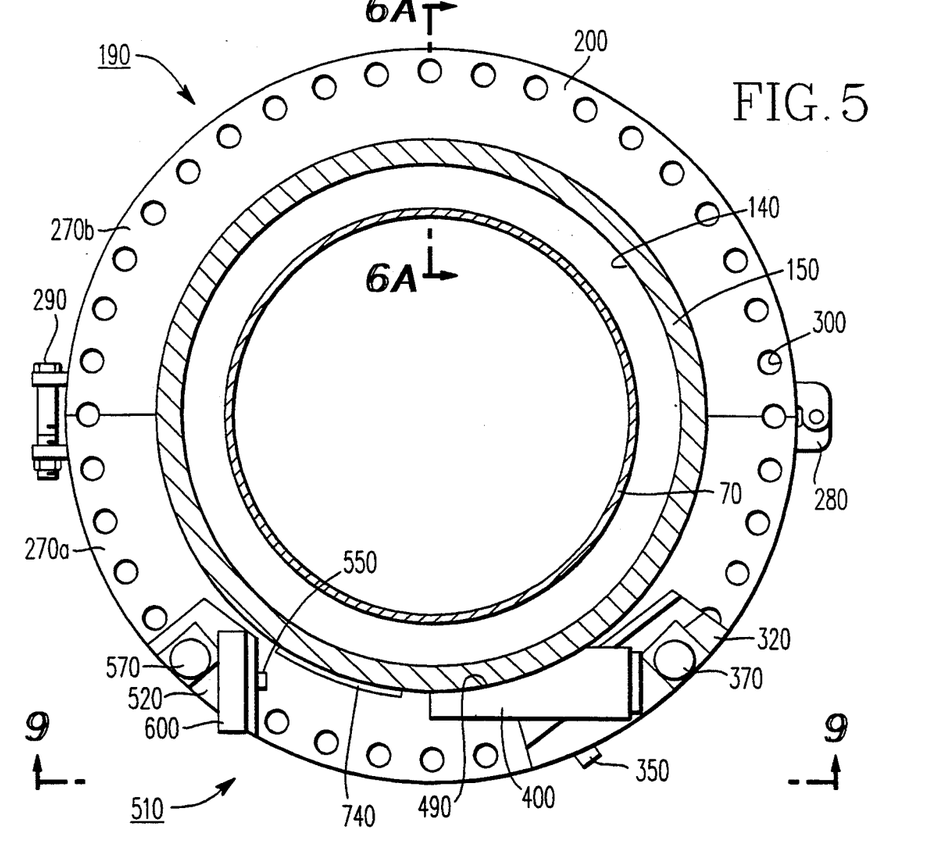
FIG. 5 is a plan view of the invention taken generally along section line 5—5 of FIG. 4.
Figure 5A:
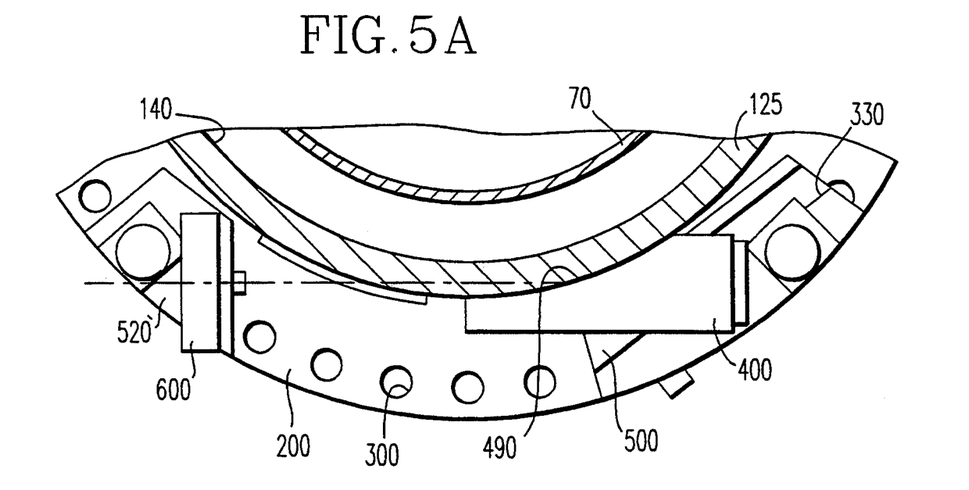
FIG. 5A is a plan view of the invention showing the path of a beam of radiation passing tangentially through the seal weld.
Figure 6:
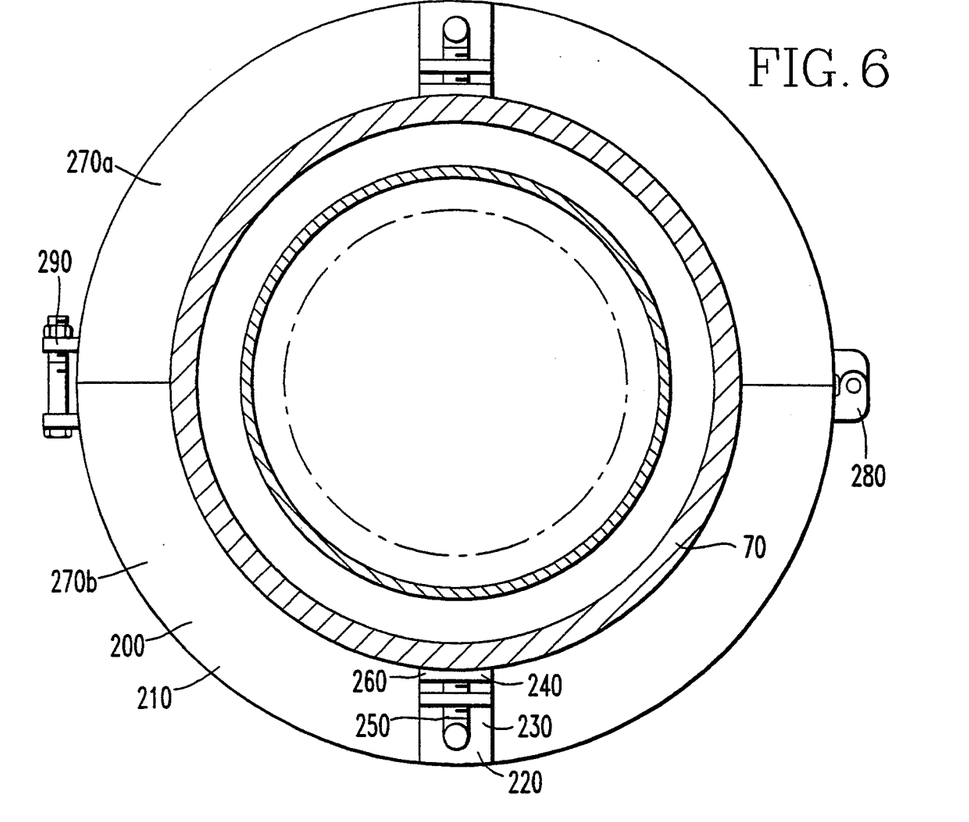
FIG. 6 is a view of the underside of the invention taken generally along section line 6—6 of FIG. 4.
Figure 6A:
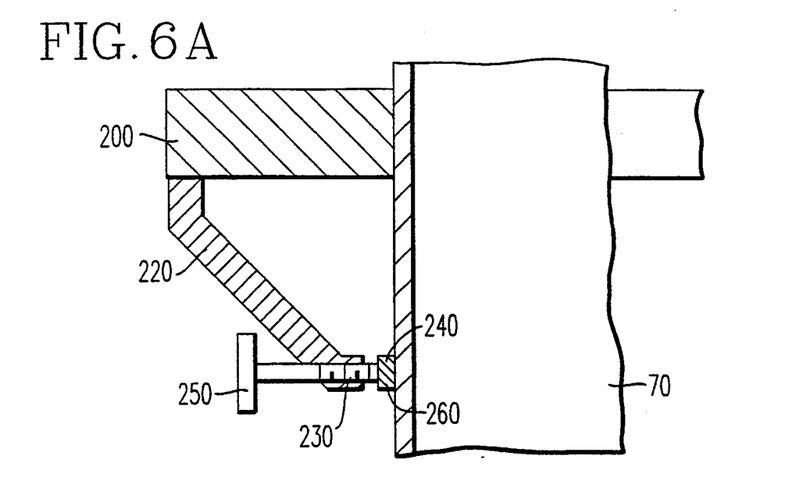
FIG. 6A is a view in partial elevation of the invention taken along section line 6A—6A of FIG. 4.
Figure 7:
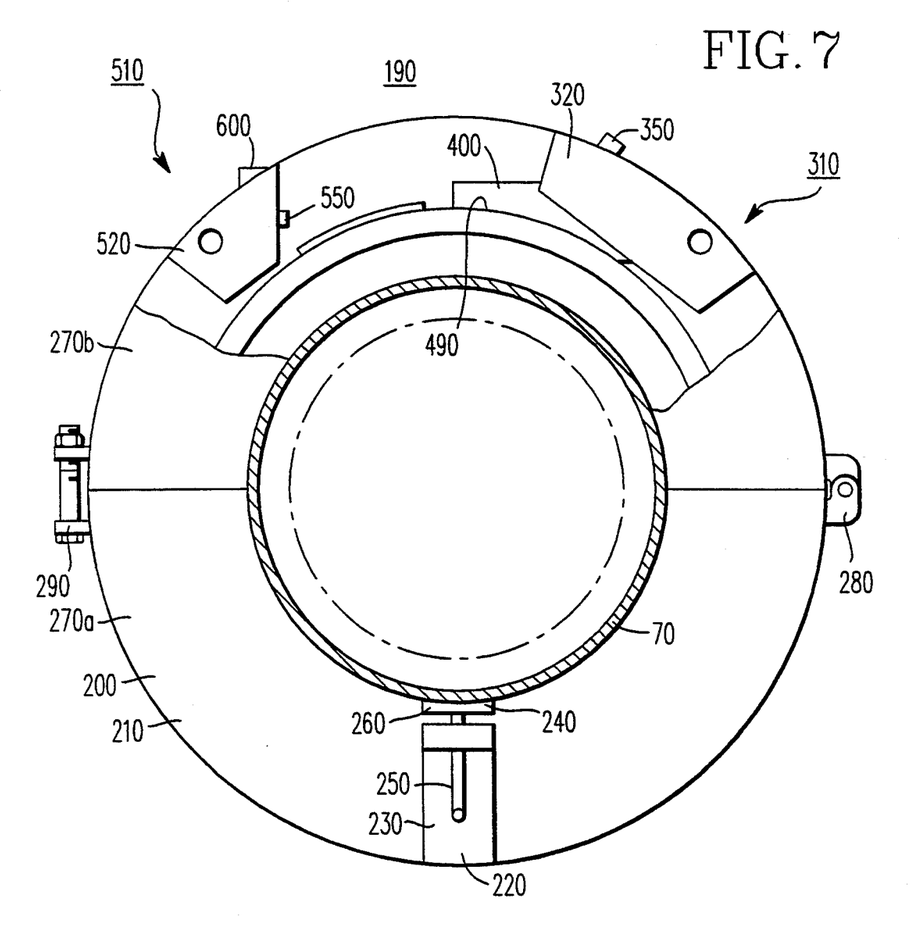
FIG. 7 is a view in partial section of the underside of the invention.
Figure 8:
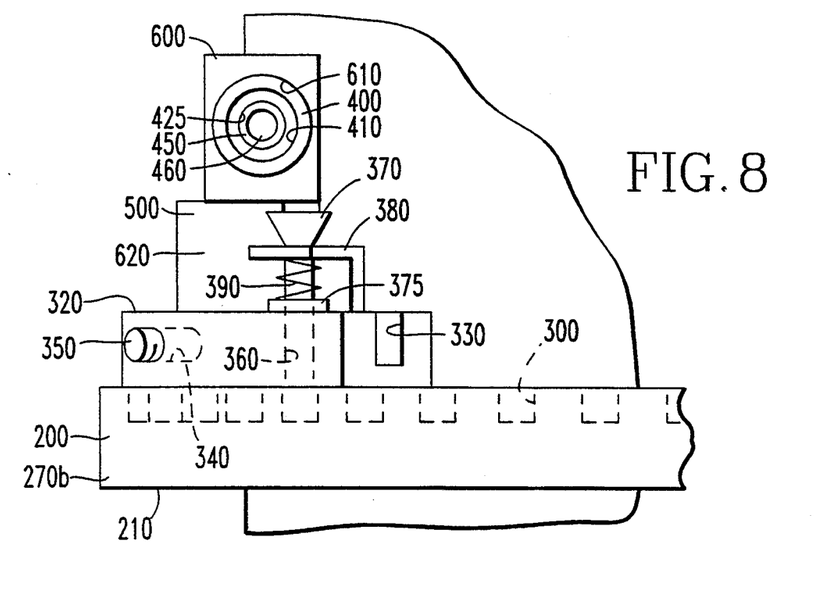
FIG. 8 is a view in elevation of a carriage and a collimator belonging to the invention, the collimator slidably engaging the carriage.
Figure 9:
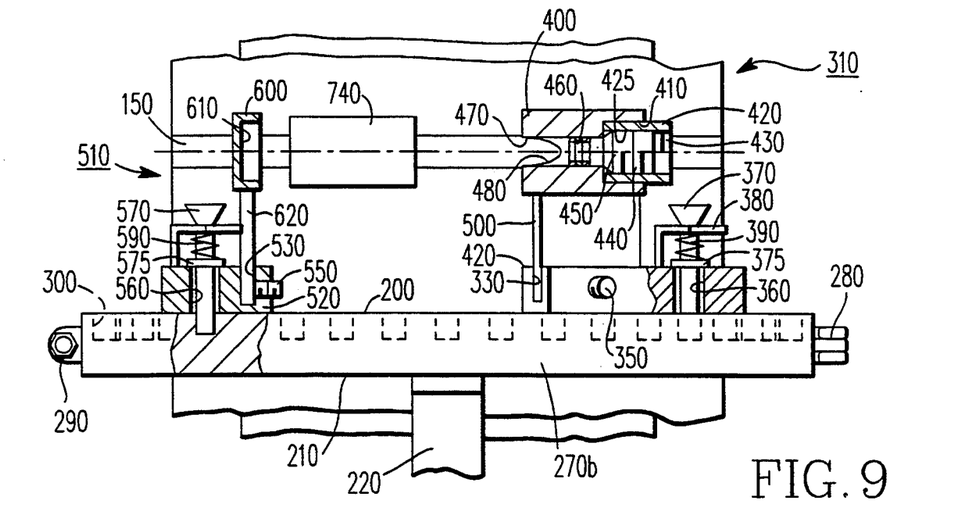
FIG. 9 is a view in partial vertical section of the invention taken along section line 9—9 of FIG. 5.

Referring to FIGS. 4, 5, 5A, 6, 7, 8 and 9, mounted atop track 200 is radiation source means, such as a radiation source assembly, generally referred to as 310, for providing a source of penetrating radiation along a predetermined axis which is illustrated by the dotted line in FIG. 5A. Radiation source assembly 310 comprises a generally rectangular-shaped, in transverse cross-section, first carriage 320 having an elongate groove 330 therein, for reasons disclosed hereinbelow. First carriage 320 also has an internally threaded bore 340 in communication with groove 330 for threadably receiving an externally threaded set screw 350. Moreover, transversely extending through first carriage 320 is a smooth bore 360 for reasons disclosed presently. Movably connected to first carriage 320 is a first pin 370 having a circumscribing ledge 375, first pin 370 being slidably received through a hole in a post 380 which is attached to first carriage 320. First pin 370 is also slidably received through bore 360. Interposed between ledge 375 and post 380 and surrounding first pin 370 may be biasing means, such as a coil spring 390, for downwardly biasing first pin 370 through bore 360 of first carriage 320 and into bore 300 of track 200, so that first carriage 320 is removably mountable on track 200. The biasing action of spring 390 ensures that as first pin 370 is biased into bore 300, first pin 370 and thus first carriage 320 will remain stationary on track 200 during the radiography process. To disengage first pin 370 from bore 300, ledge 375 is simply translated upwardly against the biasing action of spring 390 such that first pin 370 clears or disengages bore 300.

Still referring to FIGS. 4, 5, 5A 6, 7, 8, and 9, slidably connected to first carriage 320 is a collimator 400, which may be lead or depleted uranium-238, for forming a collimated beam of radiation along the predetermines axis, as disclosed more fully hereinbelow. Collimator 400 defines a generally cylindrical chamber 410 therein capable of receiving a tubular adaptor insert 420. Adaptor insert 420 is received in chamber 410 and held therein such as by a press fit. Adaptor insert 420 has a longitudinal bore 425 having internal threads 430 for threadably engaging external threads 440 of a generally cylindrical radiation source retainer 450 that is threadably secured within adaptor insert 420. Retained in retainer 450 is radiation source means, such as a radiation source 460, for providing the source of penetrating radiation, which may be gamma radiation. In the preferred embodiment of the invention, radiation source 460 is a iridium-192 isotope for providing the penetrating gamma radiation. Gamma radiation is preferred because, as well known in the art, gamma radiation is easily controllable at high intensities and therefore reduces the time required for inspections. Extending longitudinally in collimator 400 is an elongate channel 470 in communication with chamber 410 at one end of channel 470, the channel 470 terminating in a port 480 at the other end of channel 470, port 480 being formed in the exterior surface of collimator 400 for allowing the collimated beam of radiation to escape collimator 400. Although collimator 400 is generally cylindrical in shape, collimator 400 also has an inwardly curved or concave cut-away surface 490 for matingly conforming to the outwardly curved or convex surface of seal weld 150. Moreover, integrally attached to collimator 400 and outwardly extending therefrom is a slide member 500 sized to be slidably received in groove 330 of first carriage 320, so that collimator 400 is slidably adjustable with respect to first carriage 320. The previously mentioned set screw 350 engages slide member 500 in order to fix the location of slide member 500 in groove 330 once collimator 400 has been slidably adjusted to radiograph weld 150, in the manner disclosed in more detail hereinbelow.

Referring again to FIGS. 4, 5, 5A, 6, 7, 8 and 9, mounted atop track 200 is radiation shielding means, such as a radiation shielding assembly, generally referred to as 510, for shielding against the collimated beam of radiation escaping port 480 of collimator 400. Radiation shielding assembly 510 comprises a generally rectangular-shaped, in transverse cross-section, second carriage 520 having an elongate groove 530 therein for reasons disclosed hereinbelow. Second carriage 520 also has an internally threaded bore 540 in communication with groove 530 for threadably receiving an externally threaded set screw 550. Moreover, transversely extending through second carriage 520 is a smooth bore 560 for reasons disclosed presently. Movably connected to second carriage 520 is a second pin 570 having a circumscribing ledge 575, second pin 570 being slidably received through a hole in a post 580 which is attached to second carriage 520. Second pin 570 is also slidably received through bore 560. Interposed between ledge 575 and post 580 and surrounding second pin 570 may be biasing means, such as a coil spring 590, for downwardly biasing second pin 570 through bore 560 of second carriage 520 and into bore 300 of track 200, so that second carriage 520 is removably mountable on track 200. The biasing action of spring 590 ensures that as second pin 570 is biased into bore 300, second pin 570 and thus second carriage 520 will remain stationary on track 200 during the radiography process. To disengage second pin 570 from bore 300, ledge 575 is simply translated upwardly against the biasing action of spring 590, such that second pin 570 clears or disengages bore 300.

Referring yet again to FIGS. 4, 5, 5A, 6, 7, 8 and 9, slidably connected to second carriage 520 is a generally rectangular-shaped, in transverse cross-section, shield or shielding block 600, which may have a centrally disposed generally rectangular recess 610 therein. Shielding block 600 may be lead or depleted uranium-238, or the like, for providing a biological shield that absorbs or blocks the beam of radiation in order to protect any maintenance personnel located near apparatus 190. Moreover, integrally attached to shielding block 600 is a slide member 620 sized to be slidably received in groove 530 of second carriage 520, so that shielding block 600 is slidably adjustable with respect to second carriage 520. As will be understood from the above description, set screw 550 engages slide member 620 in order to fix the location of slide member 620 in groove 530 once shielding block 600 has been slidably adjusted to intercept the beam of radiation, in the manner disclosed in more detail hereinbelow.

Figure 10:
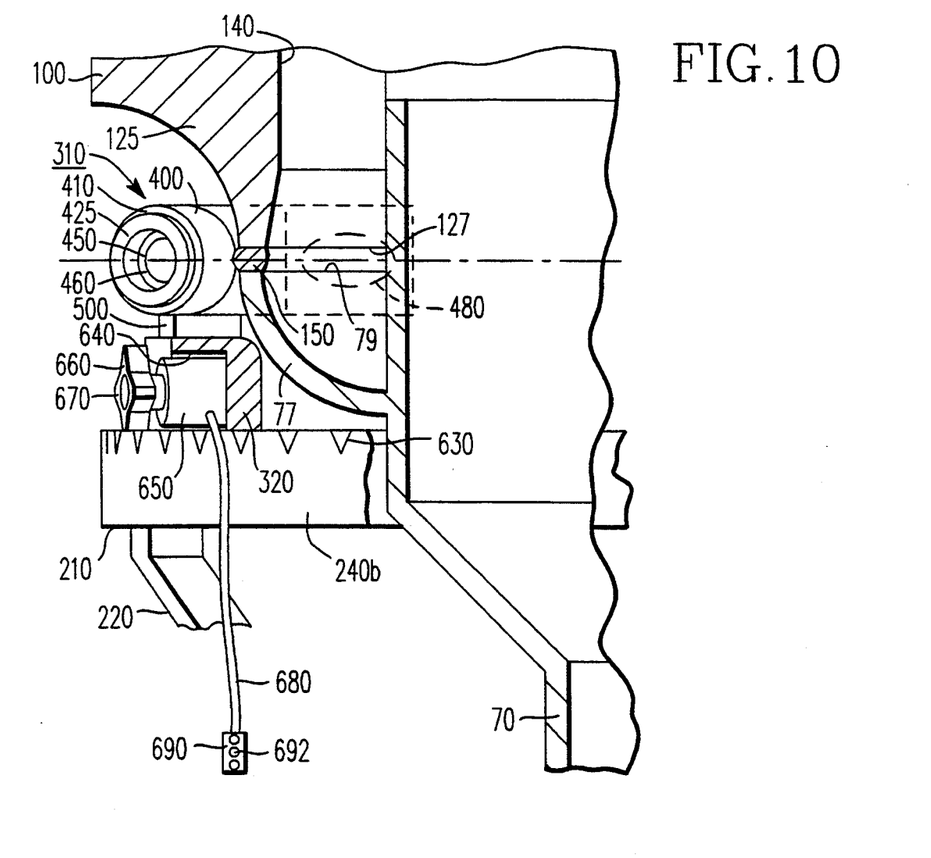
FIG. 10 is a view in partial elevation of an alternative embodiment of the invention.
Figure 11:
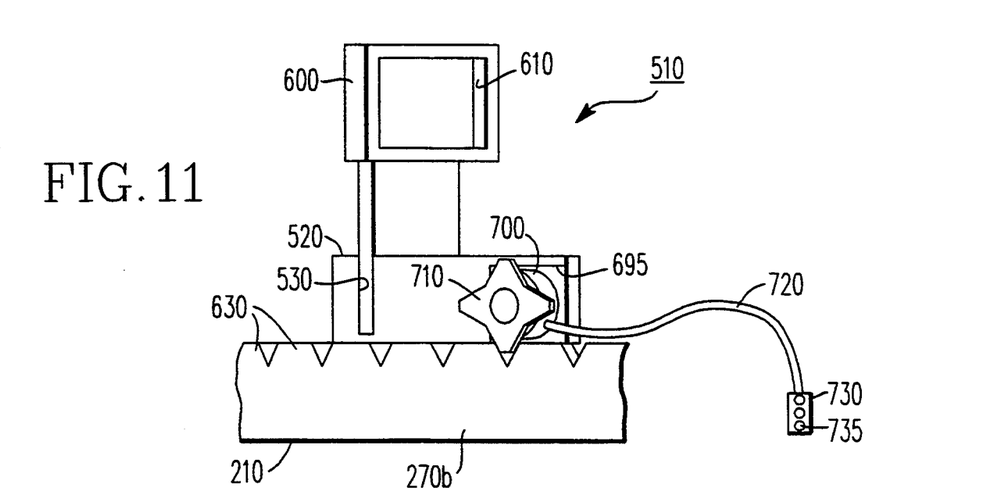
FIG. 11 is a fragmentation view in partial elevation of the alternative embodiment of the invention.
Figure 12:
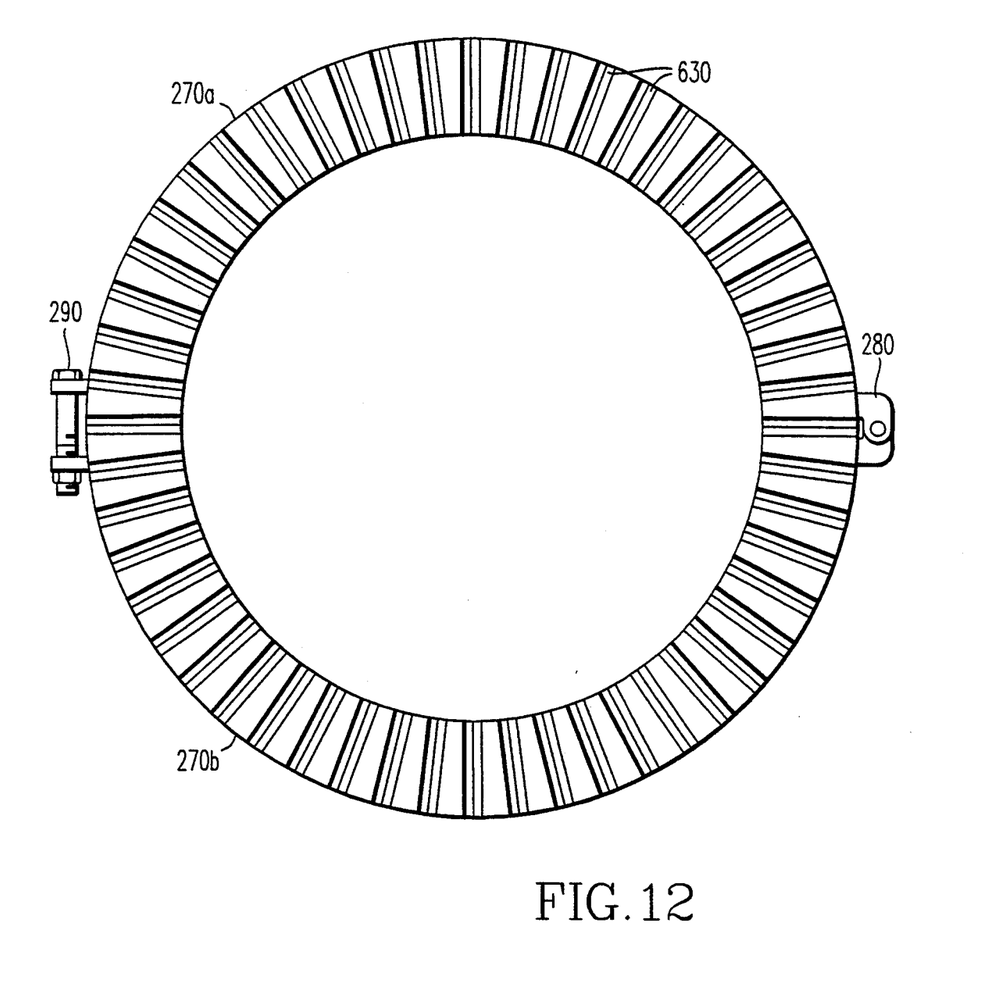
FIG. 12 is a plan view of the alternative embodiment of the track.

Referring now to FIGS. 10, 11 and 12, there is shown an alternative embodiment of the invention. In this alternative embodiment of the invention, track 200 has a plurality of gear teeth 630 integrally formed thereon and extending therearound, for reasons disclosed hereinbelow. Thus, in this alternative embodiment of the invention, track 200 does not have bores 300. Moreover, first carriage 320 has a cavity 640 therein for receiving a reversible variable speed first motor 650, which is disposed in cavity 640 and attached therein to first carriage 320. Rotatably connected to first motor 650 is a first gear wheel 660 having a plurality of gear teeth 670 therearound for engaging the gear teeth 630 of track 200. In this alternative embodiment of the invention, first carriage 320 does not have first pin 370, post 380, spring 390, and bore 360 because first gear wheel 660 fixes first carriage 320 on track 200. In addition, electrically connected to first motor 650, such as by an electrically conducting wire 680, is first control means, such as a first control unit 690, having a plurality of selectively operable control buttons 692, for energizing and deenergizing reversible first motor 650, so that radiation source assembly 310 is movable around track 200 in either direction. Moreover, second carriage 520 has a cavity 695 therein for receiving a reversible variable speed second motor 700, which is disposed in cavity 695 and attached therein to second carriage 520. Rotatably connected to second motor is a second gear wheel 710 having a plurality of gear teeth 720 therearound for engaging the gear teeth 630 of track 200. In addition, electrically connected to second motor 700, such as by an electrically conducting wire 720, is second control means, such as a second control unit 730, having a plurality of selectively operable control buttons 735, for energizing and deenergizing reversible second motor 700, so that radiation shielding assembly 510 is movable around track 200 in either direction. Thus, in this alternative embodiment of the invention, second carriage 520 does not have second pin 570, post 580, spring 590, and bore 560 because second gear wheel 701 fixes second carriage 520 on track 200.

Of course, interposed between collimator 400 and shielding block 600 and disposed externally to seal weld 150 is radiation sensitive image recording means, such as a radiographic film 740. Film 740 may be removably attached about a portion of weld 150 by any convenient means typically used in the art, such as by adhesive tape. Film 740 may be any suitable radiographic film, such a "KODAK INDUSTREX R, DR-54" film available from The Kodak Company, located in Rochester, N.Y.

Figure 13:
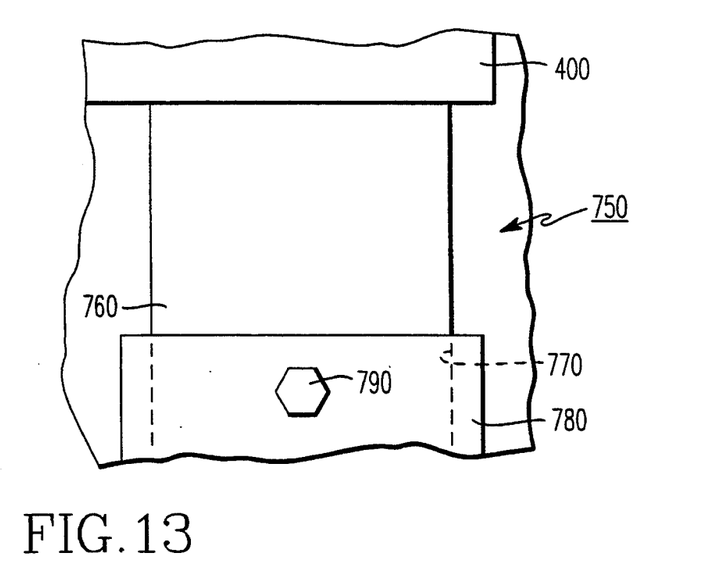
FIG. 13 is a fragmentation view in partial elevation of an alternative embodiment of a slide member attached to the collimator.

FIG. 13 illustrates an alternative embodiment of slide member 500 belonging to radiation source assembly 190. This alternative embodiment of slide member 500, generally referred to as 750, comprises a first portion 760 thereof attached to collimator 400 and slidably matingly received in a blind recess 770 formed in a second portion 780, which second portion 780 is slidably received in groove 330. In this manner, collimator 400 is capable of being slidably adjusted in recess 770 along an axis transverse to the plane of seal weld 150 (i.e., parallel to the longitudinal axis of vessel head adaptor 70). This alternative embodiment of slide member 500 further includes a set screw 790 that passes threadably through a hole in second portion 780 to engage first portion 760 in order to fix the position of second portion 780 and thus collimator 400. In this manner, collimator 400 can be precisely transversely adjusted with respect to seal weld 150.

Figure 14:
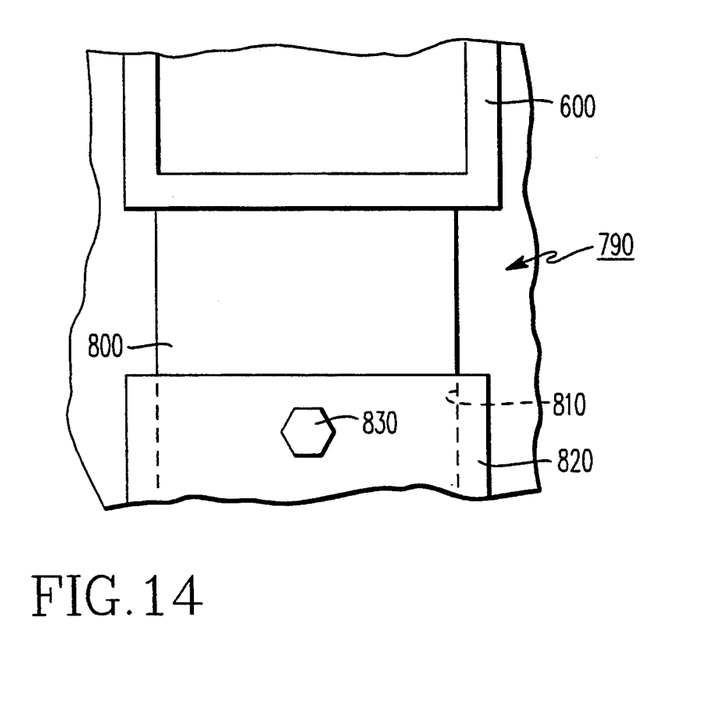
FIG. 14 is a fragmentation view in partial elevation of an alternative embodiment of a slide member attached to a shielding block belonging to the apparatus of the invention.

FIG. 14 illustrates an alternative embodiment of slide member 620 belonging to radiation shielding assembly 510. This alternative embodiment of slide member 620, generally referred to as 790, comprises a first portion 800 thereof attached to shielding block 600 and slidably matingly received in a blind recess 810 formed in a second portion 820, which second portion 820 is slidably received in groove 530. In this manner, shield block 600 is capable of being slidably adjusted in recess 810 along an axis transverse to the plane of seal weld 150 (i.e., parallel to the longitudinal axis of vessel head adaptor 70). This alternative embodiment of slide member 620 further includes a set screw 830 that passes threadably through a hole in second portion 820 to engage first portion 800 in order to fix the position of second portion 820 and thus shield block 600. In this manner, shield block 600 can be precisely transversely adjusted with respect to seal weld 150.

OPERATION

In use, the method of the invention comprises mounting track 200 on vessel head adaptor 70. This is accomplished by positioning track 200 at the desired axial location on vessel head adaptor 70 and closing segments 270a and 270b about vessel head adaptor 70 and then locking segments 270a and 270b by use of fastener 290. Next, struts 220 are removably connected to the exterior surface of vessel head adaptor 70 by adjusting screws 250. That is, foot-pads 260 are adjustably brought into abutment with the exterior surface of vessel head adaptor 70 by rotating screws 250, as needed, such that each foot-pad 260 advances into abutment with the exterior surface of vessel head adaptor 70.

Radiation source assembly 310 is mounted on track 200 for providing a source of high intensity penetrating radiation. In the preferred embodiment of the invention, radiation source assembly 310 is mounted on track 200 and removably affixed thereto by engaging first pin 370 into a preselected one of the bores 300. Radiation shielding assembly 510 may then be similarly mounted on track 200 and removably affixed thereto by engaging second pin 570 with a preselected one of the bores 300. The collimated beam of radiation emitted from port 480 of collimator 400 must pass tangentially through seal weld 150 and therefore must be aligned with seal weld 150. A course adjustment to achieve this alignment is obtained by locating radiation source assembly 310 on track 200 such that the portion of seal weld 150 to be radiographed is roughly coaxially aligned with an axis passing through port 480 of collimator 400. Radiation shielding assembly 510 is then located on track 200 such that shielding block 600 is roughly coaxially aligned with the radiation beam axis passing through port 480, in order that the center of recess 610 of shielding block 600 is normal to this axis.

The above-described adjustable features of apparatus 190 allow it to be finely adjusted in addition to being roughly adjusted in order to align port 480 and shielding block 600 tangentially with respect to the circumference of seal weld 150 for obtaining a suitable radiograph of any pinhole-sized anomalies in seal weld 150. That is, in order to obtain fine adjustment of radiation source assembly 310, slide member 500 belonging to collimator 400 is slidably moved in groove 300 until port 480 is precisely tangentially aligned with the portion of seal weld 150 to be radiographed. In this regard, port 480 is aligned with seal weld 150 such that the beam of radiation escaping collimator 400 will follow a predetermined path or axis passing tangentially through the circumference of seal weld 150. However, the beam of radiation passing through seal weld 150 should be blocked or shielded against in order to protect any maintenance personnel located nearby. In this regard, in order to obtain fine adjustment of radiation shielding assembly 510, slide member 620 belonging to shielding block 600 is slidably moved in groove 520 until shielding block 600 is coaxially aligned with port 480 to intercept the beam of radiation after it has passed through seal weld 150 and radiographic film 740 (as best seen in FIG. 5). It will be appreciated from the above description that radiation source assembly 310 and radiation shielding assembly 510 may be repositioned sequentially around the circumference of seal weld 150 for radiographing successive portions of seal weld 150 until the entire seal weld 150 is radiographed.

If use of the alternative embodiment of the invention is desired, radiation source assembly 190 and radiation shielding assembly 510 are mounted on track 200 such that gear wheels 660 and 710, respectively, engage the gear teeth 630 of track 200. Control units 690 and 730 are individually operated to selectively move radiation source assembly 190 and radiation shielding assembly 510 around track 200 such that the previously mentioned tangential alignment of port 480 and shielding block 600 with seal weld 150 is obtained. After the desired portions of seal weld 150 have been radiographed, the radiographic film 740 is removed and visually inspected in a manner well known in the art of radiograph examination to detect surface and/or subsurface seal weld anomalies.

It is important that the beam of radiation pass tangentially through seal weld 150. This is important because passing the beam of radiation tangentially, rather than perpendicularly, through seal weld 150 ensures that the beam of radiation will pass through relatively less seal weld material before encountering any seal weld anomalies. The results in a more discernable image being captured on film 740. This is so because, as well known in the art, the discernability or distinctness of the image of the anomaly captured on the radiographic film is directly proportional to the path length the radiation beam must travel through the material before encountering the anomaly. Appreciating this phenomenum is particularly important with respect to detecting relatively small pinhole-sized weld anomalies, such as found in CRDM seal welds, because a relatively large mass of weld material between the anomaly and the beam of radiation could mask the image of the anomaly on the relatively small pinhole-sized radiographic film, thereby rendering the image indistinct or completely absent.

Although the invention is fully illustrated and described herein, it is not intended that the invention as illustrated and described be limited to the details shown, because various modifications may be obtained with respect to the invention without departing form the spirit of the invention or the scope of the equivalents thereof. For example, a film cassette may be substituted for film element 740, the cassette having a roll of radiographic film therein engaged by a mechanism which advances the roll of radiographic film after each individual exposure of the film to the beam of radiation. Such a film cassette could be rigidly attached, for example, to radiation shielding assembly 510 so that the film cassette is automatically repositioned as radiation shielding assembly 510 is repositioned on the track 200. Use of such a film cassette would reduce the total time required to radiograph the entire seal weld 150 because the cassette would obviate the need to tape and untape the radiograph film to the seal weld portions to be radiographed.

Therefore, what is provided is an apparatus and a method for radiographic inspection of welds, which welds may be seal welds of the kind typically found on nuclear power reactor control rod drive mechanisms.

What is claimed is:

1. An apparatus for radiographic inspection of a weld circumscribing opposing ends of a generally tubular first member and a generally tubular second member, comprising:
(a) a track surrounding one of the members;
(b) radiation source means mounted on said track for passing a beam of radiation tangentially through the weld, said radiation source means including a collimator for collimating the radiation, so that the radiation passes tangentially through the weld;
(c) radiation shielding means mounted on said track for providing a shield against the beam of radiation; and
(d) radiation sensitive image recording means interposed between said radiation source means and said radiation shielding means and disposed adjacent the weld for capturing an image of the weld on said image recording means.

2. The apparatus of claim 1, further comprising a strut attached to said track for supporting said track on one of the members.

3. The apparatus of claim 2, wherein said track, said radiation source means, said radiation shielding means, and said image recording means are disposed exteriorly adjacent the weld.

4. On a nuclear reactor control rod drive mechanism, the control rod drive mechanism including a pressure housing having a generally tubular end portion disposed opposite and connected to a generally tubular end portion defined by a reactor pressure vessel head adaptor, an apparatus for radiographic inspection of a weld circumscribing the respective opposing end portions of the pressure housing and the head adaptor, the apparatus comprising:
(a) a generally circular track surrounding the head adaptor;
(b) a radiation source assembly mounted on said track for passing a collimated beam of radiation tangentially through a portion of the weld, said radiation source assembly including:
(i) a first carriage having a groove herein;
(ii) a collimator having an integrally attached slide member slidably engaging the groove in said first carriage, said collimator defining a chamber therein for receiving a radiation source capable of emitting radiation, and defining a channel therein in communication with the chamber at one end of the channel and terminating in a port on said collimator at the other end of the channel for collimating the radiation to form the beam of radiation, so that the beam of radiation passes tangentially through the weld;
(c) a radiation shielding assembly mounted on said track for providing a biological shield against the beam of radiation; and
(d) a radiographic film sensitive to the beam of radiation, said radiographic film interposed between said shielding block and the port on said collimator, said radiographic film disposed exteriorly of the first and second members and adjacent the weld portion for capturing an image of the weld portion as the beam of radiation passes tangentially through the weld portion.

5. The apparatus of claim 4, wherein said radiation shielding assembly comprises:
(a) a second carriage having a groove therein; and
(b) a shielding block having an integrally attached slide member slidably engaging the groove in said second carriage.

6. The apparatus of claim 5 further comprising a support structure integrally attached to said track for supporting said track on the head adaptor.

7. The apparatus of claim 6, wherein said track has a plurality of bores therein.

8. The apparatus of claim 7, further comprising:
(a) a first pin connected to said first carriage and sized to slidably engage any one of the bores in said track for removably mounting said radiation source assembly on said track; and
(b) a second pin connected to said second carriage and sized to slidably engage any one of the bores in said track for removably mounting said radiation shielding assembly on said track.

9. The apparatus of claim 6, wherein said track has a plurality of gear teeth thereon.

10. The apparatus of claim 9, further comprising:
(a) a first gear wheel rotatably connected to said first carriage and having a plurality of first gear teeth therearound for engaging the gear teeth on said track; and
(b) a second gear wheel rotatably connected to said second carriage and having a plurality of second gear teeth therearound for engaging the gear teeth on said track.

11. The apparatus of claim 10, wherein said track, said radiation source assembly, said radiation shielding assembly, and said radiographic film are disposed exteriorly adjacent the weld portion.

12. A method of radiographic inspection of a weld circumscribing opposing end portions of a tubular first member and a tubular second member, comprising the steps of:
(a) surrounding one of the members with a track;
(b) mounting a radiation source on the track so that a beam of radiation emitted by the radiation source passes tangentially through the weld, said step of mounting the radiation source on the track including the step of adjusting a collimator to collimate the beam of radiation, so that the beam of radiation passes tangentially through the weld;
(c) mounting a radiation shield on the track so that the beam of radiation is shielded against;
(d) interposing a radiation sensitive image recorder between the radiation source and the radiation shield; and
(e) disposing the radiation sensitive recorder adjacent the weld so that an image of the weld is captured on the image recorder.

13. The method of claim 12, further comprising the step of supporting the track on one of the members.

14. The method claim 13, further comprising the steps of:
(a) interposing a radiation sensitive image recorder between the radiation source and the radiation shield; and
(b) disposing the radiation sensitive image recorder adjacent the weld so that an image of the weld is captured on the image recorder.

15. A method of radiographic inspection of a weld circumscribing generally tubular opposing end portions of a first member and a second member, comprising the steps of:
(a) surrounding one of the members with a generally circular track;
(b) mounting a radiation source on the track so that a beam of radiation is generated along an axis passing tangentially through the weld, said step of mounting the radiation source on the track including the step of adjusting a collimator to collimate the beam of radiation, so that the beam of radiation passes tangentially through the weld;

(c) mounting a radiation shield on the track so that the radiation shield is disposed normal to the axis of the beam of radiation in order that the beam of radiation is shielded against; and (d) interposing a radiation sensitive radiographic film between the radiation source and the radiation shield so that the beam of radiation passes through the radiographic film; and (e) disposing the radiographic film adjacent the weld so that an image of the weld is captured on the radiographic film.

16. The method of claim 15, further comprising the step of supporting the track on one of the members by connecting a strut to the track and to the member.

17. On a nuclear reactor control rod drive mechanism having a pressure housing having a generally tubular end portion opposing a generally tubular end portion of a reactor vessel head adaptor, a method of radiographic inspection of a portion of a weld circumscribing the opposing ends of the pressure housing and head adaptor, the method comprising the steps of:

(a) removably surrounding the head adaptor with a circular track;

(b) removably mounting a radiation source assembly on the track so that a beam of radiation emitted by the radiation source assembly passes tangentially through the weld, said step of removably mounting the radiation source assembly on the track including the steps of:

(i) removably engaging a first carriage with the track, the first carriage having a groove therein; and (ii) slidably engaging a collimator in the groove of the first carriage so that the collimator is slidably adjustable in the groove of the first carriage for passing the beam of radiation tangentially through the weld;

(c) removably mounting a radiation shielding assembly on the track so that the beam of radiation is shielded against;

(d) interposing a radiation sensitive radiographic film between the collimator and the shielding block so that the axis of the beam of radiation passes through the radiographic film; and (e) disposing the radiographic film adjacent the weld portion so that an image of the weld portion is captured on the radiographic film as the beam of radiation passes through the radiographic film.

18. The method of claim 17 further comprising the step of slidably adjusting the collimator in the groove of the first carriage so that the collimated beam of radiation passes tangentially through the weld portion.

19. The method of claim 18, wherein the step of removably mounting the radiation shielding assembly on the track comprises the steps of:

(a) removably engaging a second carriage with the track, the second carriage having a groove therein; and (b) slidably engaging a shielding block in the groove of the second carriage so that the shielding block is slidably adjustable in the groove of the second carriage.

20. The method of claim 19, further comprising the step of slidably adjusting the shielding block in the groove of the second carriage so that the shielding block is disposed normal to the beam of radiation, in order that the beam of radiation is shielded against.

21. The method of claim 20, further comprising the step of supporting the track on the vessel head adaptor by connecting an elongate strut to the track and to the vessel head adaptor.

* * * * *